United States Patent
Coolidge et al.

(10) Patent No.: US 6,982,248 B2
(45) Date of Patent: Jan. 3, 2006

(54) METABOLIC INTERVENTION WITH GLP-1 TO IMPROVE THE FUNCTION OF ISCHEMIC AND REPERFUSED TISSUE

(75) Inventors: Thomas R. Coolidge, Falls Village, CT (US); Mario R. W. Ehlers, Lincoln, NE (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 396 days.

(21) Appl. No.: 09/851,738

(22) Filed: May 9, 2001

(65) Prior Publication Data

US 2002/0055460 A1 May 9, 2002

Related U.S. Application Data

(62) Division of application No. 09/302,596, filed on Apr. 30, 1999, now Pat. No. 6,284,725.
(60) Provisional application No. 60/103,498, filed on Oct. 8, 1998.

(51) Int. Cl.
*A61K 38/26* (2006.01)
*A61K 38/28* (2006.01)

(52) U.S. Cl. .................................. 514/3; 514/2; 514/21; 530/308; 530/324; 530/350; 424/198.1; 424/278.1

(58) Field of Classification Search .................... 514/2, 514/3, 21; 530/308, 324, 350; 424/198.1, 424/278.1
See application file for complete search history.

(56) References Cited

U.S. PATENT DOCUMENTS

| | | | |
|---|---|---|---|
| 4,196,196 A | | 4/1980 | Tlholtz |
| 4,976,959 A | | 12/1990 | Berger, Jr. et al. |
| 5,424,286 A | * | 6/1995 | Eng ............................... 514/2 |
| 5,955,594 A | | 9/1999 | Mishra |
| 6,107,329 A | | 8/2000 | Hoover et al. |
| 6,410,513 B1 | * | 6/2002 | Galloway et al. .............. 514/2 |
| 2002/0061838 A1 | | 5/2002 | Holmquist et al. |

FOREIGN PATENT DOCUMENTS

| WO | WO 94/15925 | 7/1994 |
|---|---|---|
| WO | WO 98/02273 | 1/1998 |
| WO | WO 98/08531 | 3/1998 |
| WO | 98/43658 | 10/1998 |
| WO | 00/16797 | 3/2000 |

OTHER PUBLICATIONS

Tibaduiza, E. C. (2001) A small molecule ligand of the glucagon–like peptide 1 receptor targets its amino–terminal hormone binding domain. J. Biol. Chem. vol. 276, pp. 37787–37793.*

Abbott et al., "The Impact of Diabetes on Survival Following Myocardial Infarction in Men vs. Women–The Framingham Study", *JAMA*, vol. 260 No. 23, pp. 3456–3460 (1988).
Bhat et al., "Skeletal Muscle Mitochondrial DNA Injury in Patients With Unilateral Peripheral Arterial Disease", *Circulation*, vol. 99, pp. 807–812 (1999).
Boska et al., "$^{31}$P MRS Studies of Exercising Human Muscle at High Temporal Resolution", *Magnetic Resonance in Medicine*, vol. 41, pp. 1145–1151 (1999).
Brand et al., "Diabetes, Intermittent Claudication, and Risk of Cardiovascular Events –The Framingham Study", Diabetes, vol. 38, pp. 504–509 (1989).
Bulllock et al., "Tissue Distribution of Messenger Ribonucleic Acid Encoding the Rat Glucagon–Like Peptide–1 Receptor", *Endocrinology*, vol. 137, No. 7, pp. 2968–2978 (1996).
Clanton et al., *"Physiological and Genomic Consequences of Intermittent Hypoxia* Invited Review: Adaptive Responses of Skeletal Muscle to Intermittent Hypoxia: the Known and the Unknown", *J. Appl. Physiol*, vol. 90, pp. 2476–2487 (2001).
Dawson et al., "A Comparison of Cilostazol and Pentoxifylline for Treating Intermittent Claudication", *The American Journal of Medicine*, vol. 109, pp. 523–530.
DuPont et al., "Marijuana and Benzodiazepines in Patients Receiving Methadone Treatment", *JAMA*, vol. 261, No. 23, pp. 3409 (1989).
Gray et al., "Risk Factor Clustering in the Insulin Resistance Syndrome–The Strong Heart Study", *American Journal of Epidemiology*, vol. 147, No. 9, pp. 869–878 (1998).
Green, "Regarding 'Phosphorus 31 Nuclear Magnetic Resonance Spectroscopy Suggests a Mitochondrial Defect in Claudicating Skeletal Muscle'", *Journal of Vascular Surgery Online*, vol. 33, No. 5, pp. 1–2 (2001).
Hamilton et al., "Insulin Reduction of Cerebral Infarction Due to Transient Focal Ischemia", *J. Neurosurg.*, vol. 82, pp. 262–268 (1995).
Hiatt et al., "Carnitine Metabolism During Exercise in Patients with Peripheral Vascular Disease", *J. Appl. Physiol.*, vol. 62, No. 6, pp. 2383–2387 (1987).
Iribarren et al., "Glycemic Control and Heart Failure Among Adult Patients with Diabetes", *Circulation*, vol. 103, pp. 2668–2673 (2001).
Irwin et al., "The Xenopus proglucagon gene encodes novel GLP–1–like peptides with insulinotropic properties", *Proc. Natl. Acad. Sci. USA*, vol. 94, pp. 7915–7920 (1997).
Matz, "Does Control of Diabetes Prevent Vascular Complication?", *JAMA*, vol. 261, No. 23, pp. 3409–3410 (1989).

(Continued)

*Primary Examiner*—Karen Cochrane Carlson
*Assistant Examiner*—Samuel W. Liu
(74) *Attorney, Agent, or Firm*—Arnold & Porter, LLP

(57) ABSTRACT

Individuals in need of treatment of ischemia-related reperfusion are treated, preferably intravenously, with a composition which includes a compound which binds to a receptor for the glucagon-like peptide-1. The invention relates to both the method and compositions for such treatment.

28 Claims, No Drawings

OTHER PUBLICATIONS

Reilly et al., "Cilostazol: Treatment of Intermittent Claudication", *The Annals of Pharmacotheraphy*, vol. 35, pp. 48–56 (2001).

Scott et al., "Glucose and Insulin Therapy in Acut Stroke; Why Delay Further?", *O J Med*, vol. 91, pp. 511–515 (1998).

Serre et al., "Exendin-(9–39) is an Inverse Agonist in the Murine Glucagon–Like Peptide–1 Receptor: Implications for Basal Intracellular Cyclic Adenosine 3', 5',–Monophosphate Levels and β–Cell Glucose Competence", *Endocrinology*, vol. 139, No. 11, pp. 4448–4454 (1998).

Sissman et al., "Patent Ductus Arteriosus, Prematurity, and Respiratory Distress Syndrome", *JAMA*, vol. 261, No. 23, pp. 3410 (1989).

Weitz et al., "Diagnosis and Treatment of Chronic Arterial Insuficiency of the Lower Extremities: A Critical Review", *Circulation*, vol. 94, pp. 3026–2049 (1996).

Partial European Search Report dated Jan. 13, 2005 issued in European Patent Application No. 04027507.5.

Apstein, C., Circulation, vol. 98, Nov. 24, 1998, pp 2223–2226.

* cited by examiner

SEQUENCE LISTING

```
<160> NUMBER OF SEQ ID NOS: 13

<210> SEQ ID NO 1
<211> LENGTH: 37
<212> TYPE: PRT
<213> ORGANISM: mammalian

<400> SEQUENCE: 1

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: mammalian

<400> SEQUENCE: 2

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: mammalian

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: mammalian

<400> SEQUENCE: 4
```

```
His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: mammalian

<400> SEQUENCE: 5

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: mammalian

<400> SEQUENCE: 6

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Gila Monster venom

<400> SEQUENCE: 7

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 31
<212> TYPE: PRT
<213> ORGANISM: Gila Monster venom

<400> SEQUENCE: 8

Asp Leu Ser Lys Gln Met Glu Glu Glu Ala Val Arg Leu Phe Ile Glu
 1               5                  10                  15

Trp Leu Lys Asn Gly Gly Pro Ser Ser Gly Ala Pro Pro Pro Ser
            20                  25                  30

<210> SEQ ID NO 9
<211> LENGTH: 39
<212> TYPE: PRT
<213> ORGANISM: Gila Monster venom

<400> SEQUENCE: 9

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30
```

```
Ser Gly Ala Pro Pro Ser
         35

<210> SEQ ID NO 10
<211> LENGTH: 38
<212> TYPE: PRT
<213> ORGANISM: Gila Monster venom

<400> SEQUENCE: 10

His Ser Asp Ala Thr Phe Thr Ala Glu Tyr Ser Lys Leu Leu Ala Lys
  1               5                  10                  15

Leu Ala Leu Gln Lys Tyr Leu Glu Ser Ile Leu Gly Ser Ser Thr Ser
             20                  25                  30

Pro Arg Pro Pro Ser Ser
         35

<210> SEQ ID NO 11
<211> LENGTH: 37
<212> TYPE: PRT
<213> ORGANISM: Gila Monster venom

<400> SEQUENCE: 11

His Ser Asp Ala Thr Phe Thr Ala Glu Tyr Ser Lys Leu Leu Ala Lys
  1               5                  10                  15

Leu Ala Leu Gln Lys Tyr Leu Glu Ser Ile Leu Gly Ser Ser Thr Ser
             20                  25                  30

Pro Arg Pro Pro Ser
         35

<210> SEQ ID NO 12
<211> LENGTH: 35
<212> TYPE: PRT
<213> ORGANISM: Gila Monster venom

<400> SEQUENCE: 12

His Ser Asp Ala Ile Phe Thr Glu Glu Tyr Ser Lys Leu Leu Ala Lys
  1               5                  10                  15

Leu Ala Leu Gln Lys Tyr Leu Ala Ser Ile Leu Gly Ser Arg Thr Ser
             20                  25                  30

Pro Pro Pro
         35

<210> SEQ ID NO 13
<211> LENGTH: 35
<212> TYPE: PRT
<213> ORGANISM: Gila Monster venom

<400> SEQUENCE: 13

His Ser Asp Ala Ile Phe Thr Gln Gln Tyr Ser Lys Leu Leu Ala Lys
  1               5                  10                  15

Leu Ala Leu Gln Lys Tyr Leu Ala Ser Ile Leu Gly Ser Arg Thr Ser
             20                  25                  30

Pro Pro Pro
         35
```

METABOLIC INTERVENTION WITH GLP-1 TO IMPROVE THE FUNCTION OF ISCHEMIC AND REPERFUSED TISSUE

CROSS REFERENCE TO A RELATED APPLICATION

This application is a divisional application of U.S. patent application Ser. No. 09/302,596 filed 30 Apr. 1999, now U.S. Pat. No. 6,284,725, which claims benefit of provisional application No. 60/103,498 filed 8 Oct. 1998.

FIELD OF THE INVENTION

This invention relates to metabolic intervention with glucagon-like peptide-1 (GLP-1) to therapeutically improve the function of ischemic and reperfused tissue.

BACKGROUND OF THE INVENTION

Cellular damage to aerobic organ tissues is well recognized as a consequence of ischemia, whether endogenous as in the case of a spontaneous coronary artery occlusion, or iatrogenic such as with open heart, coronary bypass surgery, or transplant procedures with the heart or other organs such as the lung, liver, kidney, pancreas and gastrointestinal tract. The degree and duration of the ischemia causing events are relevant to the amount of cell death and/or reversible cellular dysfunction. It is also known that much of the tissue damage in fact occurs upon reperfusion (i.e., resumption of blood flow) and re-oxygenation of the previously anoxic tissue. Reperfusion injury has been the subject of considerable recent study prompted by medical advances particularly in the treatment of reperfusion injury after myocardial infarction and other myocardial remedial procedures such as coronary bypass, other open heart surgeries, as well as organ transplants.

As a side product of normal aerobic respiration, electrons are routinely lost from the mitochondrial electron transport chain. Such electrons can react with molecular oxygen to generate the reactive free radical superoxide which through other reaction steps in the presence of hydrogen peroxide and iron produces the extraordinarily reactive and toxic hydroxyl radical. Metabolically active aerobic tissues possess defense mechanisms dedicated to degrading toxic free radicals before these reactive oxygen species can interact with cellular organelles, enzymes, or DNA, the consequences of which could, without such protective mechanisms, be cell death. These defense mechanisms include the enzymes superoxide dismutase (SOD) which disproportionates superoxide, catalase which degrades hydrogen peroxide, and the peptide glutathione which is a non-specific free radical scavenger.

While not fully understood, it is believed that with ischemia of metabolic tissues and subsequent reperfusion, a complex group of events occurs. Initially during the ischemic period, intracellular anti-oxidant enzyme activity appears to decrease, including that of SOD, catalase, and glutathione. There is also an indication that the level of xanthine oxidase activity concomitantly increases in vascular endothelial tissue during the ischemic event. The combination of enhanced ability to produce oxygen free radicals (via enhanced xanthine oxidase activity) and reduced ability to scavenge the same oxygen radicals (via reduced SOD, catalase and glutathione activity) greatly sensitizes the ischemic cell to an oxidative burst, and hence damage, should these cells be subsequently reperfused with blood and therefore oxygen. This oxidative burst occurring within seconds to minutes of reperfusion could result in reversible and irreversible damage to endothelial cells and other cells constituting the ischemic-reperfused organ matrix. If, for example, the heart is the organ under consideration, reversible oxidative damage can contribute to myocardial stunning, whereas irreversible damage presents itself as a myocardial infarction. Attendant with this initial oxidative burst is oxidation damage to cell membranes. Lipid oxidation in cell membranes appears to play a role in neutrophil chemotaxis to post-ischemic areas. Such activated neutrophils adhere to vascular endothelium, induce the conversion of xanthine dehydrogenase to xanthine oxidase within said endothelial cells, and further aggravate loss of endothelial integrity. Activated neutrophils also migrate out of the vasculature into myocardial interstitial spaces where the inflammatory cells can directly kill myocytes. Additionally; perturbations in normal calcium mobilization from sarcoplasmic reticulum as a consequence of ischemia-reperfusion contribute to reversible myocardial dysfunction referred to as myocardial stunning.

The consequences of ischemia-reperfusion events are reversible and irreversible cell damage, cell death, and decreased organ functional efficiency. More specifically, in the case of myocardial reperfusion injury, the consequences include myocardial stunning, arrhythmias, and infarction, and as a result, cariogenic shock and potentially congestive heart failure.

The paradox of cellular damage associated with a limited period of ischemic anoxia followed by reperfusion is that cell damage and death appear not only likely to directly result from the period of oxygen deprivation but, additionally, as a consequence of re-oxygenation of tissues rendered highly sensitive to oxidative damage during the ischemic period. Reperfusion damage begins with the initial oxidative burst immediately upon reflow and continues to worsen over a number of hours as inflammatory processes develop in the same post-ischemic tissues. Efforts dedicated to decreasing sensitivity of post-anoxic cells to oxidative damage and, additionally, efforts to reduce inflammatory responses in these same tissues have been shown to reduce the reversible and irreversible damage to post-anoxic reperfused organs. A combination of methods to reduce both the initial oxidative burst and subsequent inflammation associated damage could provide synergistic protection against reperfusion injury.

With respect to the treatment of ischemia coincident with myocardial infarction (MI) patients, common therapies now used are to employ thrombolytics such as streptokinase and t-PA and angioplasty. U.S. Pat. No. 4,976,959 discloses the administration of t-PA and SOD to inhibit tissue damage during reperfusion and/or percutaneous transluminal coronary angioplasty coincident with ischemia to restore regional blood flow. Thus, an increasing number of patients are being exposed to the likelihood of reperfusion injury and its effects, particularly cardiac patients.

Reperfusion injury to organs other than the heart will generally manifest itself in substantially reduced efficiency of function, a consequence of which may be premature degeneration of the organ, or simply shutdown. Additionally, transplanted organs experience enhanced rejection rates if there is significant underlying reperfusion injury.

As discussed briefly above, while the precise mechanism of reperfusion injury has not been clearly defined, mounting data, most of which has been gathered in various cardiac model studies, indicate that the generation of oxygen-derived free radicals, including superoxide anion $(O_2)^-$, the hydroxyl free radical (.OH) and $H_2O_2$, results as a consequence of the reintroduction of molecular oxygen with reperfusion and plays an important role in tissue necrosis. Agents which either decrease the production of these oxygen derived free radicals (including allopurinol and deferroxamine) or increase the degradation of these materials such as superoxide dismutase, catalase, glutathione, and copper complexes, appear to limit infarct size and also may enhance recovery of left ventricular function from cardiac stunning.

The use of metabolic intervention as a therapy specifically during acute myocardial infarction is well established, although not without controversy. There is abundant experimental and clinical evidence to support the use of a glucose-insulin-potassium (GIK) infusion—the primary form of metabolic intervention—after acute MI, particularly following the success of the Swedish Diabetes Mellitus Insulin-Glucose Infusion in Acute Myocardial Infarction (DIGAMI) study (Malmberg, K, and DIGAMI Study Group (1997) Prospective randomized study of intensive insulin treatment on long term survival after acute myocardial infarction in patients with diabetes mellitus. Brit. Med. J. 314, 1512–1515). The DIGAIMI study emphasized the efficacy of a glucose-insulin infusion for acute MI in diabetic patients, but this type of therapy has never been suggested or used for reperfusion.

It therefore can be seen that there is a need for a safe effective composition having broad applicability to prevent or ameliorate the harmful effects of ischemia and reperfusion for tissues in general, especially organ tissue and, including but not limited to myocardium. It is primary object of the present invention to fulfill this need.

Another object of the present invention is to provide a method for treating ischemia and reperfusion without the side effects normally attendant with therapies presently available.

Still another object of the present invention is to provide a pharmaceutically acceptable carrier composition which can be used for intravenous administration of the compositions of the present invention without any significant undesirable side effects and without adversely affecting antigenic or immune stimulating properties.

These and other objects and benefits of the present invention will be apparent to those skilled in the art from the further description and the accompanying claims.

SUMMARY OF THE INVENTION

Individuals in need of treatment of ischemia and/or reperfusion are treated, preferably intravenously, with a composition which includes a compound which binds to a receptor for the glucagon-like peptide-1. The invention relates to both the method and compositions for such treatment.

DETAILED DESCRIPTION OF THE INVENTION

GLP-1 is a glucose-dependent insulinotropic hormone that effectively enhances peripheral glucose uptake without inducing dangerous hypoglycemia. Further, GLP-1 strongly suppresses glucagon secretion, independent of its insuliniotropic action, and thereby powerfully reduces plasma free fatty acid (FFA) levels substantially more than can be accomplished with insulin. High FFA levels have been implicated as a major toxic mechanism during myocardial ischemia.

We have now developed the concept of GLP-1 as a metabolic therapy for ischemia-reperfusion injury. This development was based on the realization that there are two clinical situations in which ischemia-reperfusion is a routine, and potentially dangerous, event: thrombolytic procedures for acute MI, and cardiac reperfusion following ischemic cardioplegia during heart surgery. Moreover, recent experimental and clinical data have established that the phenomenon of ischemia-reperfusion is particularly responsive to metabolic therapy with GIK infusion, even more so than isolated ischemia without reperfusion (Apstein, CS (1998) Glucose-insulin-potassium for acute myocardial infarction. Remarkable results from a new prospective, randomized trial. *Circulation* 98, 2223–2226).

The two most important therapeutic advances in the treatment of acute ischemia coincident with MI in the past decade have been the introduction of thrombolysis and β-blockade. However, despite this overall success, some studies of thrombolysis have revealed an early excess mortality, which has been attributed to reperfusion-induced injury and myocardial stunning. The mechanisms underlying stunning are complex, but an emerging consensus is that this is likely related to intracellular acidosis leading to dysfunctional sarcolemmal $Ca^{2+}$ pumps and cytosolic $Ca^{2+}$ overload. The net result is impaired myocardial contractile function leading to decreased mechanical efficiency, as well as reperfusion ventricular arrhythmias. Moreover, recent research has established that the intracellular acidosis, in turn, is due to an imbalance between glycolysis and complete glucose oxidation, in the sense that the rate of glycolysis is uncoupled from the oxidation of pyruvate (the end product of glycolysis) in the TCA cycle. This uncoupling results in net $H^+$ production due to conversion of pyruvate to lactate. The most likely cause for this imbalance is the presence of high plasma free fatty acid (FFA) levels, which preferentially enter the mitochondria and inhibit pyruvate oxidation, a mechanism that elegantly accounts for the well-established observation that hearts perfused with FFA are less able to recover in the reperfusion phase than hearts perfused with glucose. It has here been discovered, and is one of the bases of this therapeutic invention that GLP-1 suppresses FFA beyond what is expected with insulin which is at the 50% level of suppression, and GLP-1 can be as high as 90% suppression of FFA.

These considerations have strengthened our conviction to treat ischemia-reperfusion with glucagon-like peptides. It is well established that during normal perfusion and adequate oxygenation, the heart depends on aerobic metabolism and uses FFAs as its preferred fuel. In contrast, during ischemia (reduced blood flow) or hypoxica (reduced $O_2$ tension), β-oxidation of fatty acids is impaired (because it is strictly aerobic) and continued provision of ATP is dependent increasingly on anaerobic glycolysis. During the ischemic period, glucose-insulin is of benefit because it enhances glucose uptake and stimulates glycolysis, thereby providing ATP for maintenance of essential membrane functions, especially ion transport. Moreover, glucose-insulin suppresses adipose tissue lipolysis, thereby reducing plasma FFA levels and uptake of FFAs into the myocardium. High levels of FFAs are toxic to the ischemic myocardium, both by direct detergent effects on membranes and increases in cAMP, and by accumulation of acylcamitine, which inhibits $Ca^{2+}$ pumps. The net effect is disturbance of ion exchange, cytosolic $Ca^{2+}$ overload, and resultant contractile dysfunction and arrhythmias.

During the reperfusion period, glucose-insulin is of benefit because, as explained above, this therapy can alleviate the metabolic imbalance that produces stunning. This is achieved by direct stimulation of PDH and hence pyruvate oxidation, and indirectly by reduced FFA uptake and hence improved ratio of pyruvate to FFA oxidation.

From the above discussion it is evident that the dual action of glucose-insulin-enhanced glucose uptake and metabolism, and reduced FFA levels—has substantial therapeutic potential in reperfusion. Some have expressed a concern that during profound, essentially zero-flow ischemia, glycolytic end products, namely lactate, will accumulate due to inadequate "wash-out". Lactate-accumulation, in turn, leads to high intracellular proton concentrations, and failure to reoxidize Nicotinamide Adenine Dinucleotide (NADH); high [$H^+$] and NADH/$NAD^+$ ratios inhibit productive glycolysis. Under these circumstances, glucose can be toxic to cells, because ATP is actually consumed in the production of fructose-1,6-bisphosphate, and high [$H^+$] can aggravate myocyte necrosis (Neely, J R, and Morgan, H E (1974) Relationship between carbohydrate and lipid metabolism and the energy balance of heart muscle. Ann. Rev. Physiol. 36,413–459). However, these concerns have not been borne out by the weight of experimental and clinical data, which indicate that glucose-insulin produces beneficial results. While not wishing to be bound by theory, the likely explanation for this is that in humans, acute spontaneous ischemia is not a condition of zero-flow ischemia, but instead represents a region of low-flow ischemia in which residual perfusion is adequate for substrate delivery and lactate washout. This realization has now provided a powerful physiological logic for the use of metabolic therapy in ischemia-reperfusion.

Modern cardiac surgery, whether involving cardiac valve replacement or coronary artery bypass grafting (CABG), routinely requires hypothermic cardioplegic arrest, aortic crossclamping, and cardiopulmonary bypass during surgery. Effectively, therefore, routine cardiac surgery induces a state of elective global ischemia followed by reperfusion, which potentially exposes the heart to all the attendant risks and injuries peculiar to myocardial ischemia-reperfusion. Hence, prevention of myocardial damage during and after cardiac operations remains a major concern. Elective cardioplegic ischemia followed by reperfusion has obvious parallels with ischemia-reperfusion encountered during acute MI followed by revascularization, and thus many of the pathophysiological principles considered in previous sections also apply during cardiac surgery. However, there are some notable differences between surgical cardioplegic ischemia-reperfusion and MI-associated ischemia-reperfusion. During surgery, the heart is arrested (cardioplegia) and infused with a cold (hypothermic) solution designed to optimize myocardial preservation. After completion of the surgery, the heart is reactivated and reperfused with oxygenated blood at body temperature. This produces a sequence of hypothermic ischemia and normothermic reperfusion, which may prevent the accumulation of high tissue levels of H+and lactate. Moreover, unlike acute MI, hypothermic cardioplegia represents a state of global, zero-flow ischemia, followed by global reperfusion.

In our previous application (Ser. No. 60/103,498), of which this is a continuation-in-part, we reviewed the disadvantages of glucose-insulin infusions and the advantages of substituting these with a GLP-1 infusion, which is safer than insulin. In summary, glucose-insulin-potassium (GIK) infusions carry significant risks of both hypoglycemia and hyperglycemia, and are technically demanding and staff-intensive. The dangers of hypoglycemia are obvious.

In contrast, these risks do not exist with a GLP-1 infusion. Glucagon-like peptide (7–36) amide (GLP-1) is a natural, gut-derived, insulinotropic peptide that constitutes a major component of the so-called incretin effect. GLP-1 exerts its major effect at the pancreatic endocrine cells, where it (1) regulates insulin expression and secretion from the β-cells in a glucose-dependent fashion; (2) stimulates the secretion of somatostatin; and (3) suppresses the secretion of glucagon from the α cells. Although not formally resolved, the strong glucagonostatic effect is presumed to result from one or all of the following: (1) direct suppression by stimulation of GLP-1 receptors on α cells, although this is unlikely; (2) paracrine suppression of glucagon secretion by intra-islet release of somatostatin; or (3) paracrine suppression by intra-islet release of insulin. Whatever the cellular mechanism, GLP-1 is unique in its capacity to simultaneously stimulate insulin secretion and inhibit glucagon release. Although a therapeutic insulin infusion also inhibits glucagon release, this effect is not as potent as that of GLP-1, which exerts a direct, intra-islet paracrine inhibition of glucagon secretion.

The dual capacity of GLP-1 to powerfully stimulate insulin release and inhibit glucagon secretion, together with the strict glucose-dependence of its insulinotropic action, endow this molecule with a unique therapeutic potential in the management of ischemia-reperfusion. First, GLP-1 strongly stimulates the secretion of endogenous insulin and therefore can be used to achieve all of the beneficial actions attributed to an insulin infusion in the metabolic treatment of ischemia-reperfusion. Although high-dose GIK infusions typically contain 25–33% glucose and 50–100 U insulin/L, the requirement for introduction of hyperglycemia per se to achieve therapeutic efficacy, versus only providing a metabolic milieu for the safe administration of high doses of insulin, is unclear. It is likely that adequate blood glucose levels are required to enable substrate delivery, but this does not necessarily imply a need for hyperglycemia and should not detract from the fact that insulin exerts important effects other than glucose uptake. Therefore, a therapeutic GLP-1 infusion will likely only require a modest (e.g., 5%) glucose coinfusion in order to maintain blood glucose at slightly above physiological levels in order to trigger insulin release. Glucose is not required as a safety measure, since blood levels of ≦3.5 mM abrogate the insulin-stimulating activity of GLP-1, thereby completely protecting against the dangers of hypoglycemia.

Second, GLP-1 exerts a powerful glucagonostatic effect, which together with its insulinotropic action will lead to a strong suppression of FFAs. One of the major benefits of glucose-insulin infusions is the reduction in circulating FFA levels and the suppression of FFA uptake. FFAs and their metabolites have direct toxic effects on the ischemic myocardium as well as during the reperfusion period, when they contribute to stunning, and hence reduction of FFA levels is a major therapeutic goal of metabolic intervention in ischemia-reperfusion, goal of metabolic intervention in ischemia-reperfusion. As glucagon is a powerful stimulus for adipose tissue lipolysis and FFA production, GLP-1 mediated glucagon suppression further augments the insulin-induced reduction in circulating FFAs. Thus, GLP-1 therapy is superior to a glucose-insulin infusion in this regard. Indeed, preliminary data in healthy volunteers indicate that an intravenous GLP-1 infusion will reduce fasting plasma FFA levels to <10% of control values.

GLP-1 should be effective in the majority of patients without requiring concurrent glucose administration. However, a small proportion of subjects may require glucose/GLP-1 to elicit an adequate insulin response. In addition, it also may be necessary to administer potassium to correct excess shifts of potassium in the intracellular compartment when glucose is co-administered with GLP-1.

In addition to GLP-1 or its biological analogues, the therapy can include use of free radical scavengers such as glutathione, melatonin, Vitamin E, and superoxide dismutase (SOD). In such combinations reperfusion damage risk is lessened even further.

The term "GLP-1", or glucagon-like peptide, includes mimetics, and as used in the context of the present invention can be comprised of glucagon-like peptides and related peptides and analogs of glucagon-like peptide-1 that bind to a glucagon-like peptide-1 (GLP-1) receptor protein such as the GLP-1 (7–36) amide receptor protein and has a corresponding biological effect on insulin secretion as GLP-1 (7–36) amide, which is a native, biologically active form of GLP-1. See Goke, B and Byrne, M, *Diabetic Medicine*, 1996, 13:854–860. The GLP-1 receptors are cell-surface proteins found, for example, on insulin-producing pancreatic β-cells. Glucagon-like peptides and analogs will include species having insulinotropic activity and that are agonists of, i.e. activate, the GLP-1 receptor molecule and its second messenger activity on, inter alia, insulin producing β-cells. Agonists of glucagon-like peptide that exhibit activity through this receptor have been described: EP 0708179A2; Hjorth, S. A. et al., *J. Biol. Chem.* 269 (48):30121–30124 (1994); Siegel, E. G. et al. Amer. Diabetes Assoc. 57th Scientific Sessions, Boston (1997); Hareter, A. et al. Amer. Diabetes Assoc. 57th Scientific Sessions, Boston (1997); Adelhorst, K. et al. *J. Biol. Chem.* 269(9):6275–6278 (1994); Deacon C. F. et al. 16th International Diabetes Federation Congress Abstracts, *Diabetologia Supplement* (1997); Irwin, D. M. et al., *Proc. Natl. Acad. Sci. USA*. 94:7915–7920 (1997); Mosjov, S., *Int. J. Peptide Protein Res.* 40:333–343 (1992). Glucagon-like molecules include polynucleotides that express agonists of GLP-1, i.e. activators of the GLP-1 receptor molecule and its secondary messenger activity found on, inter alia, insulin-producing β-cells. GLP-1 mimetics that also are agonists include, for example, chemical compounds specifically designed to activate the GLP-1 receptor. Glucagon-like peptide-1 antagonists are also known, for example see e.g. Watanabe, Y et al., *J. Endocrinol.* 140(1):45–52 (1994), and include exendin (9–39) amine, an exendin analog, which is a potent antagonist of GLP-1 receptors (see, e.g. WO97/46584). Recent publications disclose Black Widow GLP-1 and Ser[2] GLP-1, see G. G. Holz, J. F. Hakner/*Comparative Biochemistry and Physiology*, Part B 121(1998)177–184 and Ritzel, et al., *A synthetic glucagon-like peptide-1 analog with improved plasma stability*, J.Endocrinol 1998 October 159(1):93–102.

Further embodiments include chemically synthesized glucagon-like polypeptides as well as any polypeptides or fragments thereof which are substantially homologous. "Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 50 percent homology, and preferably greater than 90 percent homology, equivalent biological activity in enhancing β-cell responses to plasma glucose levels, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

Mammalian GLP peptides and glucagon are encoded by the same gene. In the ileum the phenotype is processed into two major classes of GLP peptide hormones, namely GLP-1 and GLP-2. There are four GLP-1 related peptides known which are processed from the phenotypic peptides. GLP-1 (1–37) has the sequence His Asp Glu Phe Glu Arg His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:1). GLP-1 (1–37) is amidated by post-translational processing to yield GLP-1 (1–36) $NH_2$ which has the sequence His Asp Glu Phe Glu Arg His Ala Glu Gly Thr Phe Thr Ser Asp Val Ser Ser Tyr Leu Glu Gly Gin Ala Ala Lys Glu Phe Ile Ala Trp Leu Val Lys Gly Arg ($NH_2$) (SEQ ID NO:2); or is enzymatically processed to yield GLP-1 (7–37) which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:3). GLP-1 (7–37) can also be amidated to yield GLP-1 (7–36) amide which is the natural form of the GLP-1 molecule, and which has the sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:4) and in the natural form of the GLP-1 molecule.

Intestinal L cells secrete GLP-1 (7–37) (SEQ ID NO:3) and GLP-1 (7–36) $NH_2$ (SEQ ID NO:4) in a ratio of 1 to 5, respectively. These truncated forms of GLP-1 have short half-lives in situ, i.e., less than 10 minutes, and are inactivated by an aminodipeptidase IV to yield Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5); and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6), respectively. The peptides Glu Gly Thr Phe Thr Ser Asp Val Ser Ser Tyr Leu Glu Gly Gln Ala Ala Lys Glu Phe Ile Ala Trp Leu Val Lys Gly Arg Gly (SEQ ID NO:5): and Glu Gly Thr Phe Thr Ser Asp Val Ser Ser Tyr Leu Glu Gly Gln Ala Ala Lys Glu Phe Ile Ala Trp Leu Val Lys Gly Arg ($NH_2$) (SEQ ID NO:6), have been speculated to affect hepatic glucose production, but do not stimulate the production or release of insulin from the pancreas.

There are six peptides in Gila monster venoms that are homologous to GLP-1. Their sequences are compared to the sequence of GLP-1 in Table 1.

TABLE 1 a. H A E G T F T S D V S S Y L E G Q A A K E F I A W L V K G R $NH_2$
b. H S D G T F T S D L S K Q M E E E A V R L F I E W L K N G G P S S G A P P P S $NH_2$
c.          D L S K Q M E E E A V R L E T E W L K N G G P S S G A P P P S $NH_2$
d. H G E G T F T S D L S K Q M E E E A V R L F I E W L K N G G P S S G A P P P S $NH_2$
e. H S D A T F T A E Y S K L L A K L A L Q K Y L E S I L G S S T S P R P P S S
f. H S D A T F T A E Y S K L L A K L A L Q K Y L E S I L G S S T S P R P P S

TABLE 1-continued g. H S D A I F T E E Y S K L L A K L A L Q K Y L A S I L G S R T S P P P NH₂
h. H S D A I F T Q Q Y S K L L A K L A L Q K Y L A S I L G S R T S P P P NH₂ a = GLP-1 (SEQ ID NO:4)
b = Exendin 3 (SEQ ID NO:7).
c = Exendin 4 (9–39(NH₂(SEQ ID NO:8)).
d = Exendin 4 (SEQ ID NO:9).
e = Helospectin I (SEQ ID NO:10).
f = Helospectin II (SEQ ID NO:11).
g = Helodermin (SEQ ID NO:12).
h = $Q^8$, $Q^9$ Helodermin (SEQ ID No:13).

The major homologies as indicated by the outlined areas in Table 1 are: peptides c and h are derived from b and g, respectively. All 6 naturally occurring peptides (a, b, d, e, f and g) are homologous in positions 1, 7, 11 and 18. GLP-1 and exendins 3 and 4 (a, b and d) are further homologous in positions 4, 5, 6, 8, 9, 15, 22, 23, 25, 26 and 29. In position 2, A, S and G are structurally similar. In position 3, residues D and E (Asp and Glu) are structurally similar. In positions 22 and 23 F (Phe) and I (Ile) are structurally similar to Y (Tyr) and L (Leu), respectively. Likewise, in position 26 L and I are structurally equivalent.

Thus, of the 30 residues of GLP-1, exendins 3 and 4 are identical in 15 positions and equivalent in 5 additional positions. The only positions where radical structural changes are evident are at residues 16, 17, 19, 21, 24, 27, 28 and 30. Exendins also have 9 extra residues at the carboxyl terminus.

The GLP-1 like peptides can be made by solid state chemical peptide synthesis. GLP-1 can also be made by conventional recombinant techniques using standard procedures described in, for example, Sambrook and Maniaitis. "Recombinant," as used herein, means that a protein is derived from recombinant (e.g., microbial or mammalian) expression systems which can be genetically modified to contain an expression gene for GLP-1 or its biologically active analogues.

The GLP-1 like peptides can be recovered and purified from recombinant cell cultures by methods including, but not limited to, ammonium sulfate or ethanol) precipitation, acid extraction, anion or cation exchange chromatography, phosphocellulose chromatography, hydrophobic interaction chromatography, affinity chromatography, hydroxylapatite chromatography and lectin chromatography. High performance liquid chromatography (HPLC) can be employed for final purification steps.

The polypeptides of the present invention may be a naturally purified product, or a product of chemical synthetic procedures, or produced by recombinant techniques from prokaryotic or eukaryotic hosts (for example by bacteria, yeast, higher plant, insect and mammalian cells in culture or in vivo). Depending on the host employed in a recombinant production procedure, the polypeptides of the present invention are generally non-glycosylated, but may be glycosylated.

GLP-1 activity can be determined by standard methods, in general, by receptor-binding activity screening procedures which involve providing appropriate cells that express the GLP-1 receptor on their surface, for example, insulinoma cell lines such as RINmSF cells or INS-1 cells. See also Mosjov, S.(1992) and EP0708170A2. In addition to measuring specific binding of tracer to membrane using radio-immunoassay methods, cAMP activity or glucose dependent insulin production can also be measured. In one method, a polynucleotide encoding the receptor of the present invention is employed to transfect cells to thereby express the GLP-1 receptor protein. Thus, for example, these methods may be employed for screening for a receptor agonist by contacting such cells with compounds to be screened and determining whether such compounds generate a signal, i.e. activate the receptor.

Polyclonal and monoclonal antibodies can be utilized to detect, purify and identify GLP-1 like peptides for use in the methods described herein. Antibodies such as ABGA1178 detect intact unspliced GLP-1 (1–37) or N-terminally-truncated GLP-1 (7–37) or (7–36) amide. Other antibodies detect on the very end of the C-terminus of the precursor molecule, a procedure which allows by subtraction to calculate the amount of biologically active truncated peptide, i.e. GLP-1 (7–37) or (7–36) amide (Orskov et al. Diabetes, 1993, 42:658–661; Orskov et al. J. Clin. Invest. 1991, 87:415–423).

Other screening techniques include the use of cells which express the GLP-1 receptor, for example, transfected CHO cells, in a system which measures extracellular pH or ionic changes caused by receptor activation. For example, potential agonists may be contacted with a cell which expresses the GLP-1 protein receptor and a second messenger response, e.g. signal transduction or ionic or pH changes, may be measured to determine whether the potential agonist is effective.

The glucagon-like peptide-1 receptor binding proteins of the present invention may be used in combination with a suitable pharmaceutical carrier. Such compositions comprise a therapeutically effective amount of the polypeptide, and a pharmaceutically acceptable carrier or excipient. Such a carrier includes, but is not limited to, saline, buffered saline, dextrose, water, glycerol, ethanol, lactose, phosphate, mannitol, arginine, trehalose and combinations thereof. The formulations should suit the mode of administration and are readily ascertained by those of skill in the art. The GLP-1 peptide may also be used in combination with agents known in the art that enhance the half-life in vivo of the peptide in order to enhance or prolong the biological activity of the peptide. For example, a molecule or chemical moiety may be covalently linked to the composition of the present invention before administration thereof. Alternatively, the enhancing agent may be administered concurrently with the composition. Still further, the agent may comprise a molecule that is known to inhibit the enzymatic degradation of GLP-1 like peptides may be administered concurrently with or after administration of the GLP-1 peptide composition. Such a molecule may be administered, for example, orally or by injection.

Patients administered GLP-1 or its analogues in combination with the carrier systems here enumerated, especially those treated before a planned event or within the first 4 hours after an ischemic event, are observed to have less arrhythmia, less tissue damage, and less discomfort without side effects.

From these considerations it is evident that an infusion of GLP-1 can be expected to exert a major therapeutic effect in myocardial reperfusion. It is expected that GLP-1 can be administered either by I.V. or subcutaneous administration for continuous infusion by intravenous (I.V.) 0.1 pmol/kg/min to 10 pmol/kg/min and by subcutaneous (S.C.) 0.1 pmol/kg/min to 75 pmol/kg/min, and for single injection (bolus) by I.V. 0.005 nmol/kg to 20 nmol/kg and S.C. 0.1 nmol/kg to 100 nmol/kg are suitable levels of administration. The GLP-1 infusion can be coadministered with glucose (5%) if required to maintain blood glucose levels ≧5 mM (to maintain efficient insulin secretion). Similarly, coadministration of potassium ($K^+$) will also be considered, depending on the extent to which activation of the membrane $Na^+/K^+$ ATPase leads to a shift of $K^+$ into the intracellular space. The GLP-1 treatment will be commenced as early in the post-ischemic period as possible after, for example, acute spontaneous ischemia in the home or ambulance context and before reperfusion therapies, and continued thereafter. In the case of cardiac surgery, the GLP-1 infusion should commence 12–24 hours prior to surgery, during surgery from the onset of anesthesia until aortic crossclamping, and immediately after unclamping for a period of at least 72 hours postoperatively. As earlier explained, co-administration of a free radical scavenger will further aid reperfusion recovery.

From the above it can be seen that the invention accomplishes all of its stated objectives.

What is claimed is:

1. A method for preventing or ameliorating a decrease in a function of a tissue, wherein the tissue has undergone an ischemia-reperfusion event sufficient to cause cell death, or reversible or irreversible cell damage in said tissue, comprising administering to an individual an effective amount of a composition comprising a compound that activates a receptor for glucagon-like peptide-1 (GLP-1) in a pharmaceutical carrier.

2. The method of claim 1 wherein the compound is a GLP-1 (7–36) amide or a biologically active analog thereof.

3. The method of claim 1 wherein the pharmaceutical carrier is selected from the group consisting of saline, buffered saline, dextrose, water, glycerol, ethanol, lactose, phosphate, mannitol, arginine, treholose, and combinations thereof.

4. The method of claim 1 wherein administering to the individual-is at a dose level of 0.1 pmol/kg/min to 10 pmol/kg/min.

5. The method of claim 1 wherein there is concurrent administration of glucose.

6. The method of claim 1 wherein administration commences within 4 hours of an ischemic event.

7. The method of claim 6 wherein administration occurs within 4 hours and is a continuous infusion of the composition.

8. The method of claim 1 wherein the isehemic-reperfusion event arises from a medical procedure that is a surgical event selected from the group consisting of cardiac surgical procedures, organ transplants, traumatic limb amputation and reattachment.

9. The method of claim 1 wherein the ischemic-reperfusion event is concurrent with a gut infarct or a myocardial infarct.

10. The method of claim 1 comprising reperfusion therapy.

11. A method for preventing or ameliorating a decrease in a function of a tissue, wherein the tissue has undergone an ischemia-reperfusion event sufficient to cause cell death, or reversible or irreversible cell damage in said tissue, comprising administering to an individual an effective amount of an exendin.

12. The method of claim 11, wherein the exendin is administered at a dose of 0.005 nmol/kg to 20 nmol/kg.

13. The method of claim 11 wherein the pharmaceutical carrier is selected from the group consisting of saline, buffered saline, dextrose, water, glycerol, ethanol, lactose, phosphate, mannitol, arginine, treholose, and combinations thereof.

14. The method of claim 11 wherein there is concurrent administration of glucose.

15. The method of claim 11 wherein administration commences within 4 hours of an ischemic event.

16. The method of claim 11 wherein administration occurs within 4 hours of an ischemic event and is a continuous infusion.

17. The method of claim 11 wherein the ischemic-reperfusion event arises from a medical procedure that is a surgical event selected from the group consisting of cardiac surgical procedures, organ transplants and traumatic limb amputation and reattachment.

18. The method of claim 11 wherein the ischemia-reperfusion event is concurrent with a gut infarct or a myocardial infarct.

19. The method of claim 11, further comprising administering an anti-inflammatory agent.

20. The method of claim 1, further comprising administering an anti-inflammatory agent.

21. The method of claim 11, wherein the exendin is exendin 3 or exendin 4.

22. The method of claim 11 comprising reperfusion therapy.

23. A method for preventing or ameliorating tissue injury caused by reperfusion of blood flow following a period of ischemia, comprising administering to an individual an effective amount of a compound that activates a receptor for glucagon-like peptide-1.

24. The method of claim 23 wherein the period of ischemia is caused by an event selected from the group consisting of cardiac surgical procedures, organ transplants, and traumatic limb amputation and reattachment.

25. The method of claim 23 further comprising administering an anti-inflammatory agent.

26. The method of claim 23 wherein there is concurrent administration of any one of glucose, potassium or free radical scavenger.

27. The method of claim 23 wherein administration is by subcutaneous or micropressure injection, deep lung insufflation, external or implant pump, depot injection, and other sustained release mechanisms, oral deliver and patch, buccal and other cross skin and membrane mechanism.

28. The method of claim 23 comprising reperfusion therapy.

* * * * *

UNITED STATES PATENT AND TRADEMARK OFFICE
CERTIFICATE OF CORRECTION

PATENT NO. : 6,982,248 B2 Page 1 of 1
DATED : January 3, 2006
INVENTOR(S) : Thomas R. Coolidge et al.

It is certified that error appears in the above-identified patent and that said Letters Patent is hereby corrected as shown below:

<u>Column 17,</u>
Line 17, delete the hyphen between "individual" and "is".
Line 26, delete "isehemic" and replace with -- ischemic --.

Signed and Sealed this

Fourth Day of April, 2006

JON W. DUDAS
*Director of the United States Patent and Trademark Office*